US00PP11512P

United States Patent [19]

Danziger

[11] Patent Number: Plant 11,512

[45] Date of Patent: Sep. 19, 2000

[54] *TORENIA* PLANT NAMED 'DANTOPKMN'

[75] Inventor: Gabriel Danziger, Nir Zvi, Israel

[73] Assignee: Danziger "Dan" Flower Farm, Post Beit Dagan, Israel

[21] Appl. No.: 09/100,312

[22] Filed: Jun. 19, 1998

[51] Int. Cl.[7] ..... A01H 5/00

[52] U.S. Cl. ..... Plt./263

[58] Field of Search ..... Plt./263

[56] References Cited

U.S. PATENT DOCUMENTS

P.P. 10,118 11/1997 Miyazaki et al. ..... Plt./263

P.P. 10,843 3/1999 Tamura et al. ..... Plt./263

*Primary Examiner*—Lynette R. F. Smith
*Assistant Examiner*—Wendy A Baker
*Attorney, Agent, or Firm*—Foley & Lardner

[57] ABSTRACT

A new and distinct cultivar of *Torenia* plant named 'Dantopkmn' characterized by its tubular-shaped flower consisting of four petals in which the top petal is white, the two side petals are of a violet color and the bottom petal is light violet with yellow lengthways strips; its ability to grow quickly and flower almost year round; its cascading growth habit; its ability to perform well in partial shade; its recommended growing temperature range of 15–25° C.; and its dense branching which gracefully cascades from hanging baskets.

1 Drawing Sheet

BACKGROUND OF THE INVENTION

The present invention comprises a new and distinct cultivar of *Torenia* known by the cultivar name 'Dantopkmn'.

'Dantopkmn' is a natural color bud mutation which arose within a population of *Torenia* 'Blue Moon' plants(unpatented) in Moshav Mishmar Hashiva, Israel in 1997. The mutant was discovered by the inventor Gabriel Danziger in April 1997 in a controlled environment in Mishmar Hashiva, Israel.

The first act of asexual reproduction of 'Dantopkmn' was accomplished when vegetative cuttings were taken from the mutant in May 1997 in a controlled environment in Mishmar Hashiva by a technician working under supervision of the inventor. Horticultural examination of selected units initiated in July 1997 has demonstrated that the combination of characteristics as herein disclosed for 'Dantopkmn' are firmly fixed and are retained through successive generations of asexual reproduction.

'Dantopkmn' has not been observed under all possible environmental conditions. The phenotype may vary somewhat with variations in environment such as temperature, light intensity and day length, however, without any variations in genotype. The following observations, measurements and comparisons described the plants grown in Mishmar Hashiva under greenhouse conditions which approximate those generally used in commercial practice.

BRIEF DESCRIPTION OF THE INVENTION

The following traits have been repeatedly observed and are determined to be basic characteristics of 'Dantopkmn' which in combination distinguish this *Torenia* as a new and distinct cultivar:

1. A tubular flower consisting of four petals: a top white petal, two violet side petals, and a light violet bottom petal with yellow lengthwise stripes.
2. The flower is 35 mm in length.
3. Almost year-round flowering.
4. Cascading growth habit, pinching is needed.
5. Evergreen, perennial, herbaceous plant.
6. Performs best in partial shade.
7. Recommended temperature range is 15–25° C.

8. Needs constant fertilization and irrigation.
9. Densely branched plant, gracefully cascading from hanging baskets.
10. Fast growing plant.

Of the commercial cultivars known to the inventors, the most similar in comparison to 'Dantopkmn' is *Torenia* 'Summer Wave Pink', (unpatented). In comparison to 'Summer Wave Pink', 'Dantopkmn' has more intense color of flowers and foliage, bigger flowers and leaves, improved vigor, and is adapted better for outdoor growth.

BRIEF DESCRIPTION OF THE DRAWING

The accompanying color photographic sheet shows typical flower and foliage characteristics of 'Dantopkmn', with the color being as true as possible with illustrations of this type. The photograph does not accurately depict the color values of the leaf and flower.

DETAILED BOTANICAL DESCRIPTION

In the following description color references are made to The Royal Horticultural Society Colour Chart. The color values were determined between 10:00 a.m. and 12:00 p.m. on April 1998 under full sunlight at Mishmar Hashiva.

Classification:

*Botanical.*—A hybrid of *Scrophulariaceae Torenia fournieri hybrida.*

*Commercial.*—*Torenia* cultivar 'Dantopkmnn'.

Plant:

*Growth habit.*—Cascading; freely and densely branched.

*Plant height.*—15 cm.

*Spreading area.*—60 cm.

*Blooming period.*—Almost all year round.

*Lastingness of individual bloom.*—5 days.

Stem:

*Thickness.*—3 mm.

*Color.*—Yellow-green, R.H.S. 146-B.

*Pubescence.*—Medium.

*Branching.*—Strong.

*Length of internode.*—6 cm.

Leaf:

*Arrangement on stem*.—Opposite.

*Shape*.—Oval.

*Size*.—Length of 4 cm; Width of 3.5 cm.

*Thickness*.—1 mm.

*Color of upper surface*.—yellow-green R.H.S. 146-A.

*Color of lower surface*.—Yellow-green R.H.S. 146-A.

*Margin*.—Serrate.

*Markings*.—None.

*Pubescence*.—Weak.

Flower:

*Orientation at opening*.—Upward.

*Type*.—Single.

*Shape*.—Tubular.

*Diameter*.—35 mm.

*Length of corolla tube*.—Approximately 23 mm.

*Color of outer corolla tube*.—R.H.S. 146-B.

*Number of Sepals*.—4.

*Color*.—White, R.H.S. 155-C with purple violet R.H.S. 82-A top petal is pale purplish pink nearly white, outer corolla tube is R.H.S. 84A and the lower petal is light pinkish R.H.S. 82B, lower stripes on lower petal R.H.S. 3A.

*Peduncle*.—25 mm in length and color is yellow-green R.H.S. 146-B.

*Color of calyx*.—R.H.S. 146-B.

*Reproductive organs*.—Pistil: One in number and color is violet R.H.S. 84-B. Stamens (number): 4. Anther (color): White 155-A. Filament (color): White 155-C. Seed fruit set: None observed. Fragrance: None.

I claim:

1. A new and distinct cultivar of *Torenia* plant named 'Dantopkmn', substantially as shown and described.

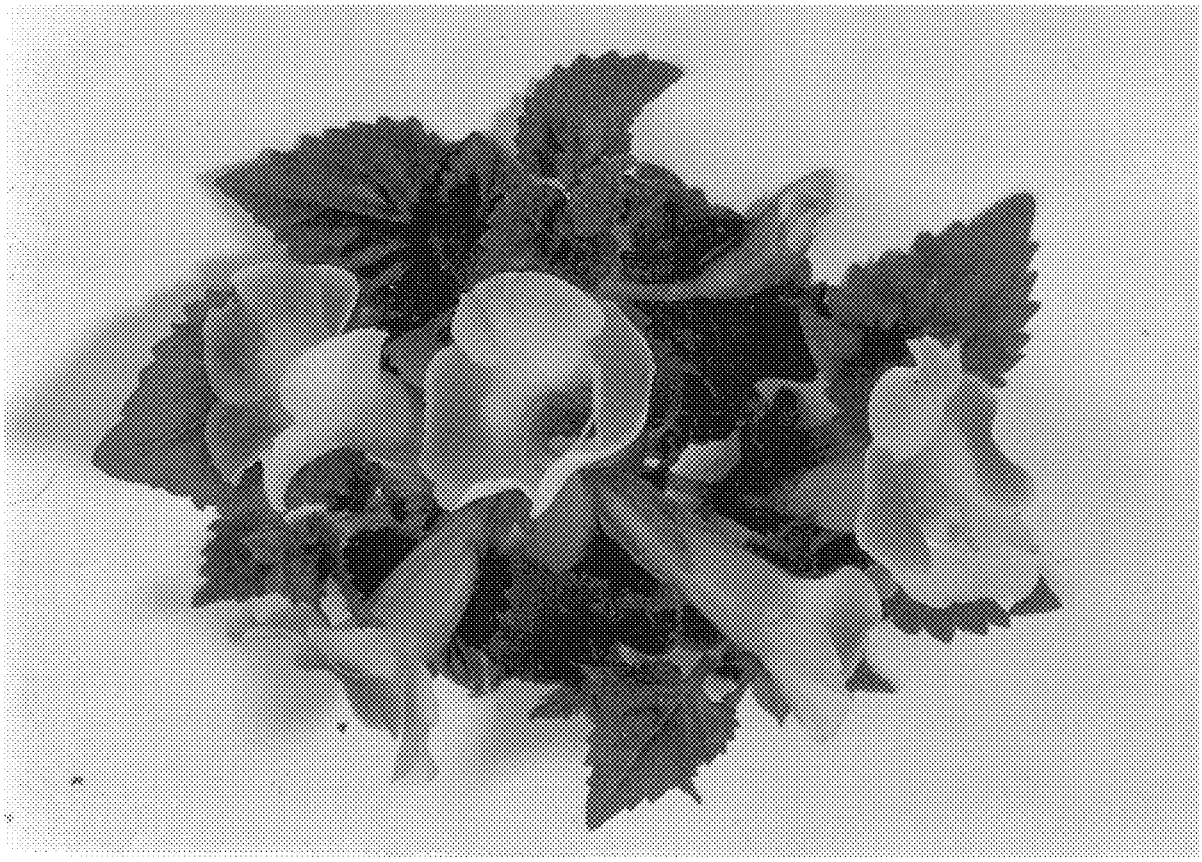

* * * * *